United States Patent
Glazer

(10) Patent No.: US 10,898,238 B2
(45) Date of Patent: Jan. 26, 2021

(54) TRANSLATIONAL INSTRUMENTATION FOR SPONDYLOLISTHESIS AND SCOLIOSIS REDUCTION

(71) Applicant: Tenzin LLC, Chestnut Hill, MA (US)

(72) Inventor: Paul Glazer, Boston, MA (US)

(73) Assignee: Tenzin LLC, Chestnut Hill, MA (US)

( * ) Notice: Subject to any disclaimer, the term of this patent is extended or adjusted under 35 U.S.C. 154(b) by 212 days.

(21) Appl. No.: 16/237,385

(22) Filed: Dec. 31, 2018

(65) Prior Publication Data
US 2019/0133647 A1 May 9, 2019

Related U.S. Application Data

(60) Division of application No. 15/362,165, filed on Nov. 28, 2016, now Pat. No. 10,166,048, which is a continuation-in-part of application No. 14/569,218, filed on Dec. 12, 2014, now abandoned, which is a division of application No. 13/287,811, filed on Nov. 2, 2011, now Pat. No. 8,936,599.

(51) Int. Cl.
| | |
|---|---|
| *A61B 17/02* | (2006.01) |
| *A61B 17/70* | (2006.01) |
| *A61F 2/44* | (2006.01) |
| *A61F 2/30* | (2006.01) |

(52) U.S. Cl.
CPC ........ *A61B 17/7077* (2013.01); *A61B 17/025* (2013.01); *A61F 2/4455* (2013.01); *A61B 2017/0256* (2013.01); *A61F 2002/30616* (2013.01)

(58) Field of Classification Search
CPC ............................................. A61B 2017/0256
See application file for complete search history.

(56) References Cited

U.S. PATENT DOCUMENTS

| 1,493,729 A | 5/1924 | Brown |
|---|---|---|
| 3,973,895 A | 8/1976 | Hayashi |
| 4,411,106 A | 10/1983 | Fleckenstein et al. |
| 4,957,495 A | 9/1990 | Kluger |
| D321,464 S | 11/1991 | Mikiya |
| 5,104,281 A | 4/1992 | Corvi |
| 5,601,556 A | 2/1997 | Pisharodi |

(Continued)

OTHER PUBLICATIONS

Non-Final Office Action dated Nov. 27, 2013 issued during the prosecution of U.S. Appl. No. 13/287,811 (11 pages).

(Continued)

*Primary Examiner* — David W Bates
(74) *Attorney, Agent, or Firm* — Locke Lord LLP; Joshua L. Jones; Alicia J. Carroll

(57) ABSTRACT

An instrument for spinal procedures is a vertebral endplate spreader device having a vertebral endplate spreader and a driver handle. The vertebral endplate spreader includes a linkage with a drive sprocket operatively connected for rotation relative thereto and with a secondary sprocket. The secondary sprocket is operatively connected for rotation relative to the linkage. The vertebral endplate spreader includes a belt operatively connected to the drive sprocket and the secondary sprocket to be driven about a belt axis. The driver handle has a distal end and a proximal end. The distal end is operatively connected to the drive sprocket to actuate rotation of the belt.

8 Claims, 16 Drawing Sheets

(56) References Cited

U.S. PATENT DOCUMENTS

| | | |
|---|---|---|
| 5,864,746 A | 1/1999 | Chang |
| 5,938,551 A | 8/1999 | Warner |
| 6,168,601 B1 | 1/2001 | Martini |
| 6,558,392 B1 | 5/2003 | Martini |
| 7,744,649 B2 | 6/2010 | Moore |
| 7,811,288 B2 | 10/2010 | Jones et al. |
| 7,988,700 B2 | 8/2011 | Shluzas et al. |
| 8,007,517 B2 | 8/2011 | Lins et al. |
| 8,353,963 B2 | 1/2013 | Glerum |
| 2005/0245928 A1 | 11/2005 | Colleran et al. |
| 2007/0055274 A1 | 3/2007 | Appenzeller et al. |
| 2007/0100340 A1 | 5/2007 | Lange et al. |
| 2007/0149978 A1 | 6/2007 | Shezifi et al. |
| 2007/0191856 A1 | 8/2007 | Gil et al. |
| 2010/0049204 A1 | 2/2010 | Soubeiran |
| 2010/0249792 A1 | 9/2010 | Bonvallet et al. |
| 2010/0274252 A1 | 10/2010 | Bottomley et al. |
| 2011/0077655 A1 | 3/2011 | Fisher et al. |
| 2011/0270258 A1* | 11/2011 | Johnson ............. A61B 17/1624 606/90 |

OTHER PUBLICATIONS

Final Office Action dated May 22, 2014 issued during the prosecution of U.S. Appl. No. 13/287,811 (10 pages).

Non-Final Office Action dated Jul. 27, 2016 issued during the prosecution of U.S. Appl. No. 14/569,218 (8 pages).

* cited by examiner

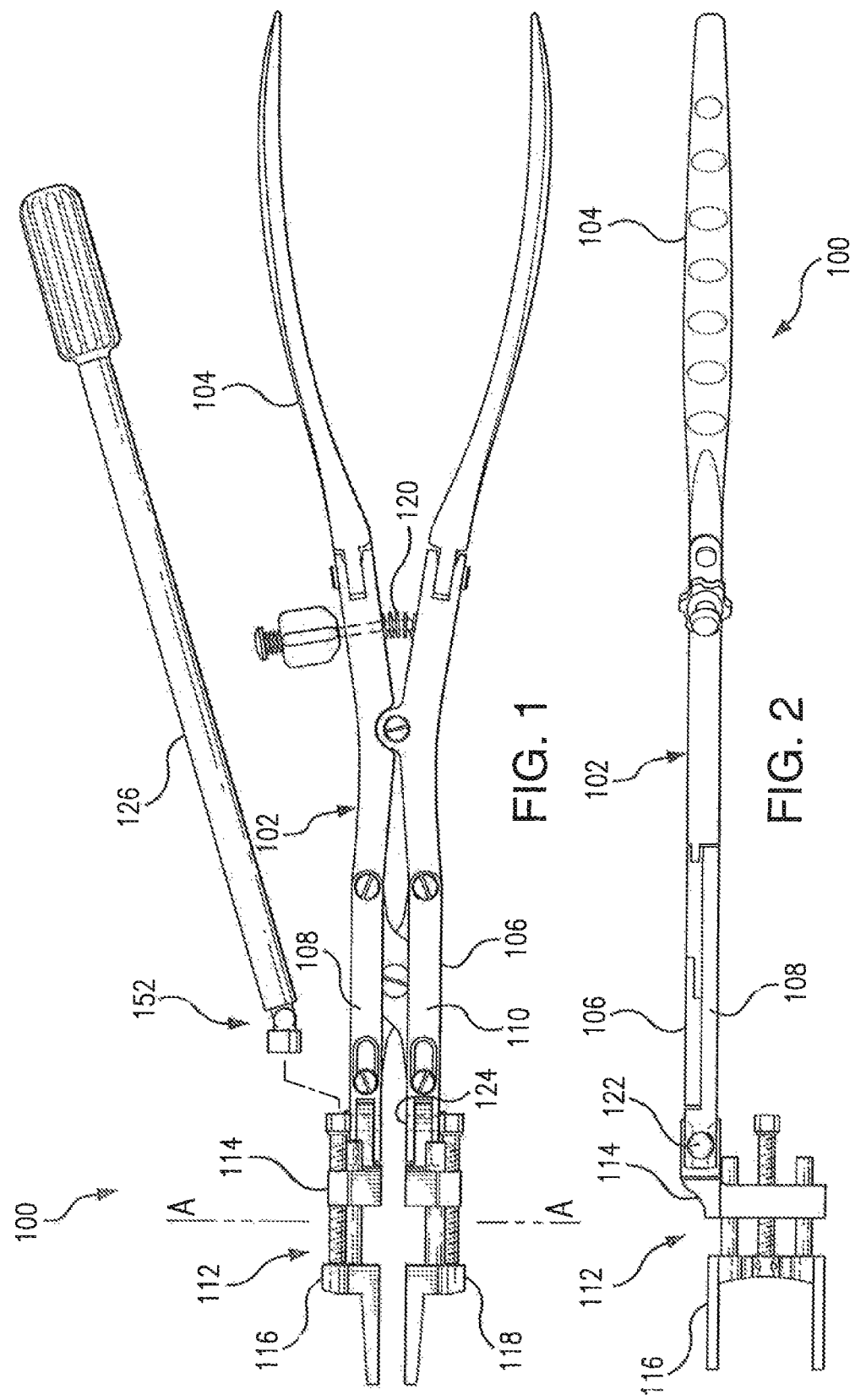

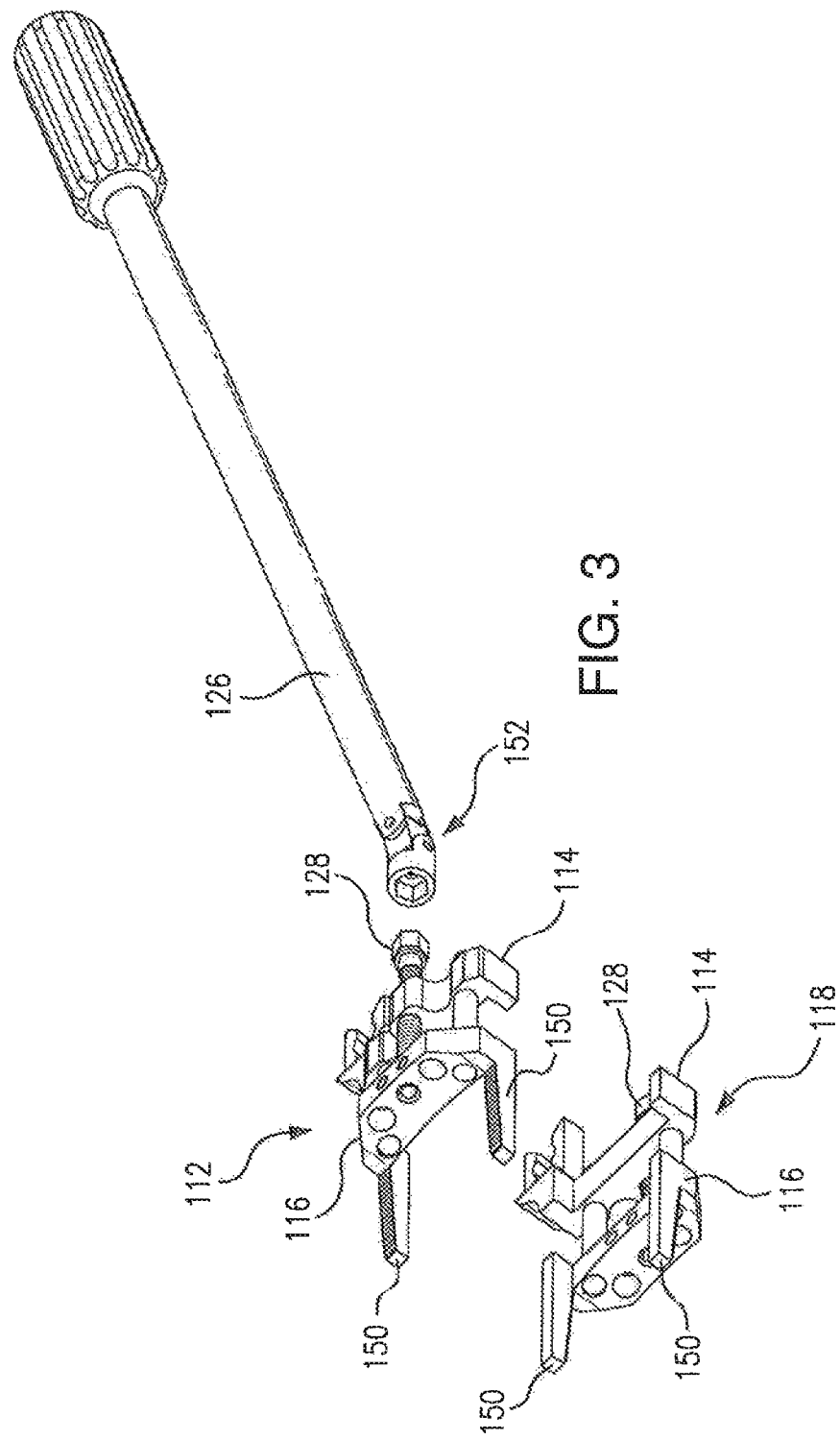

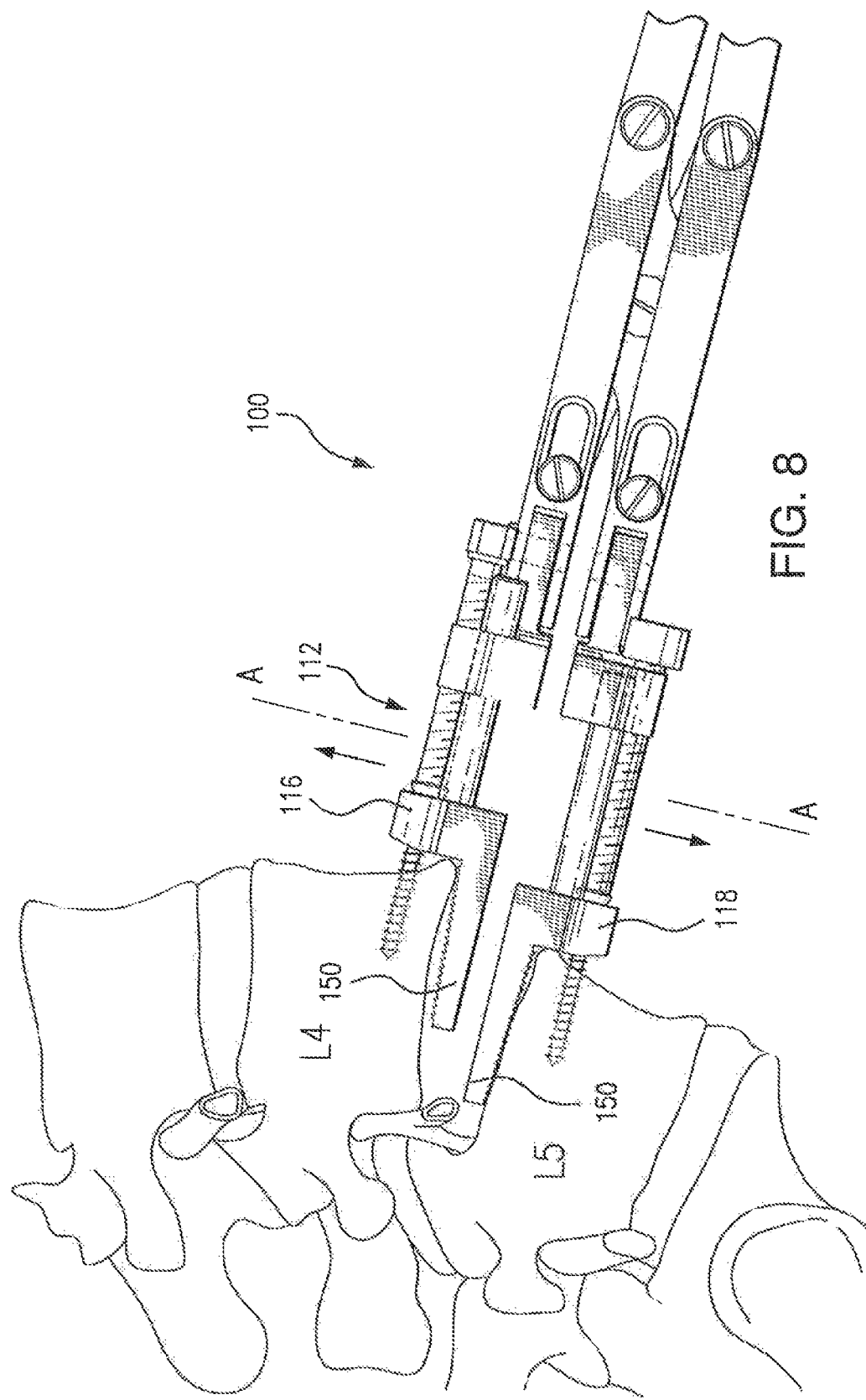

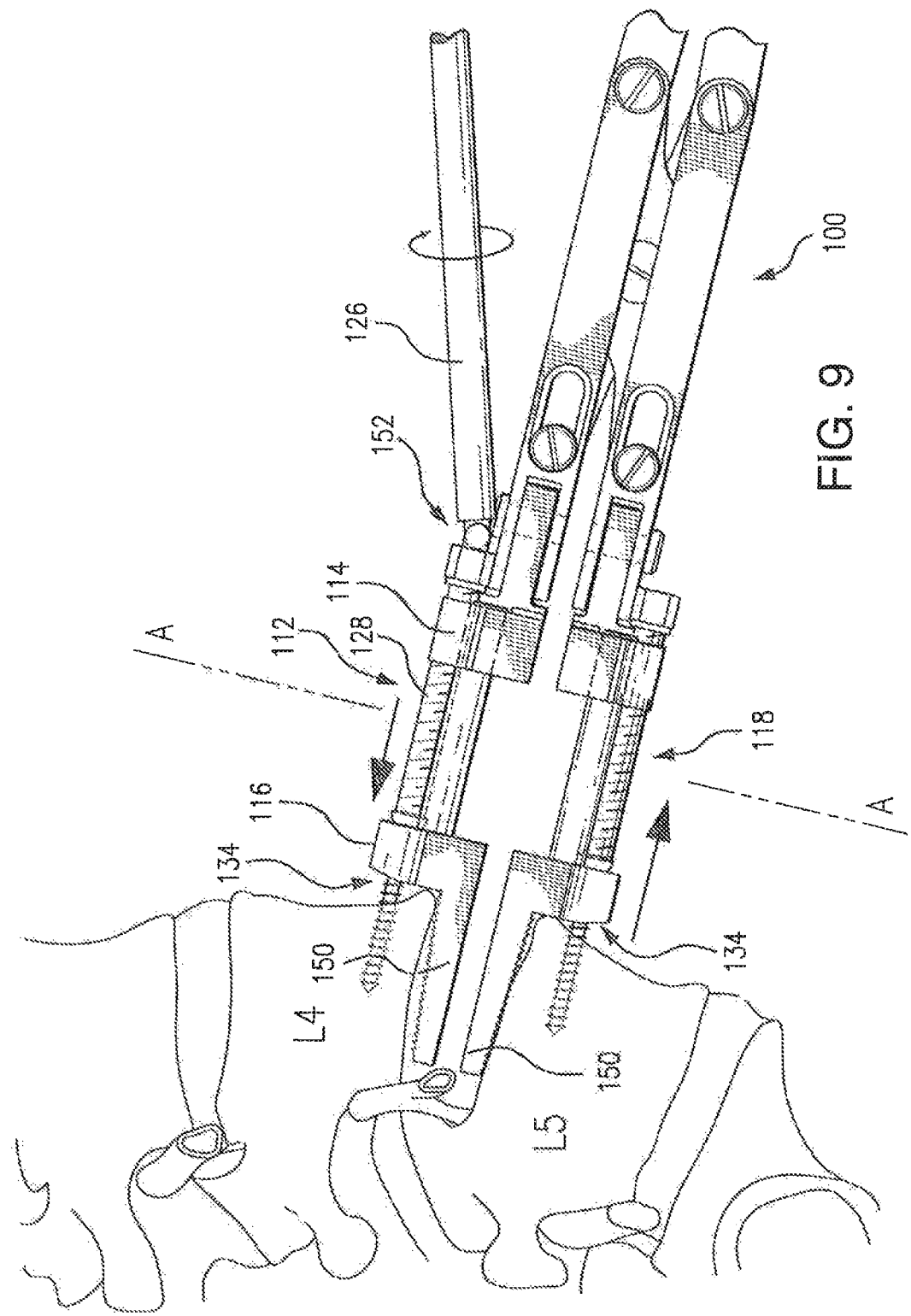

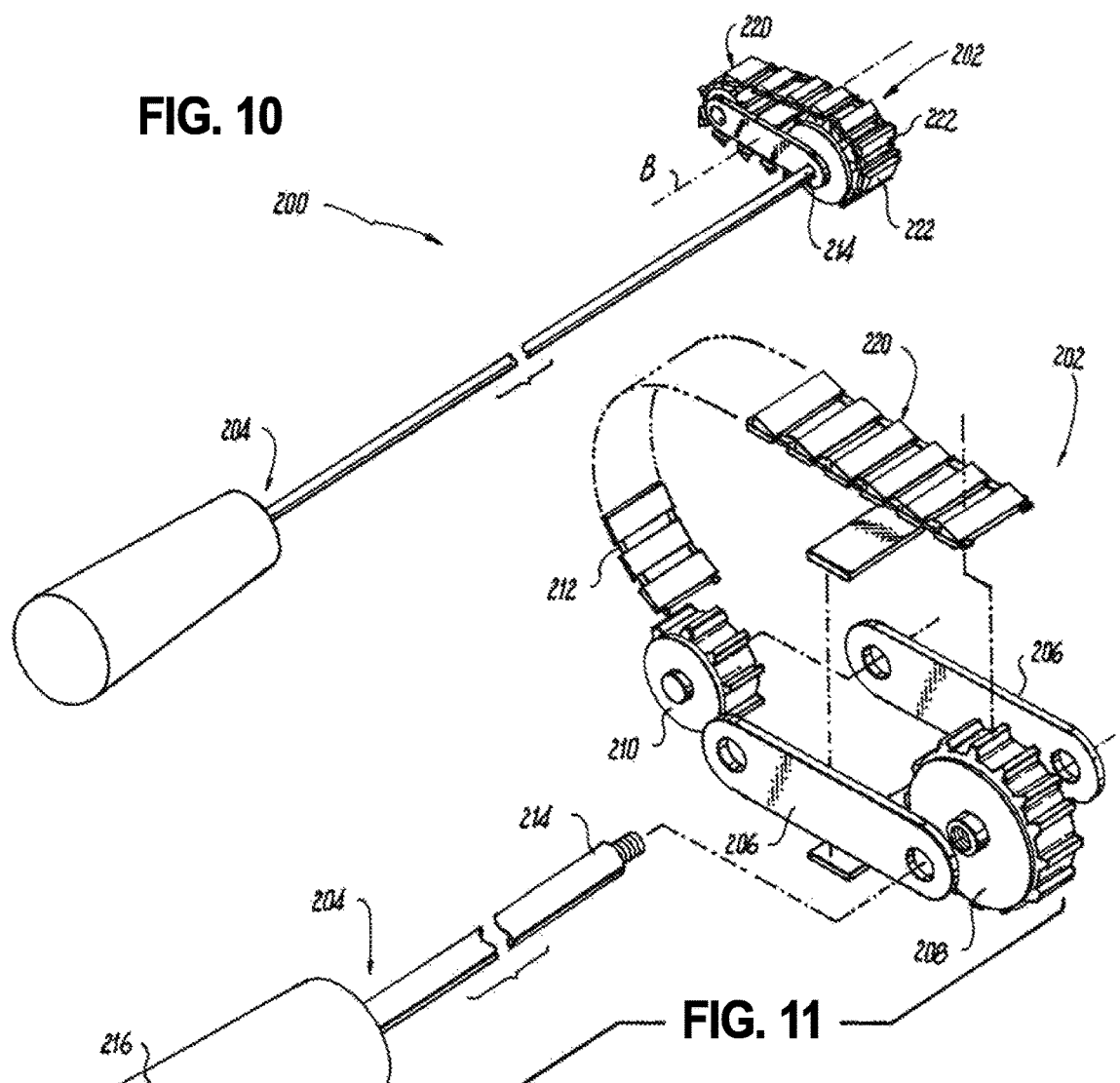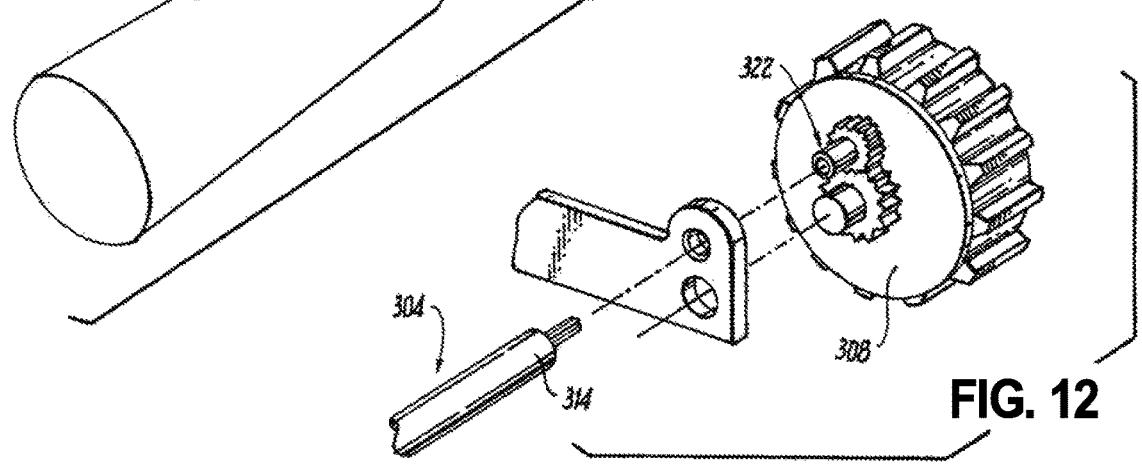

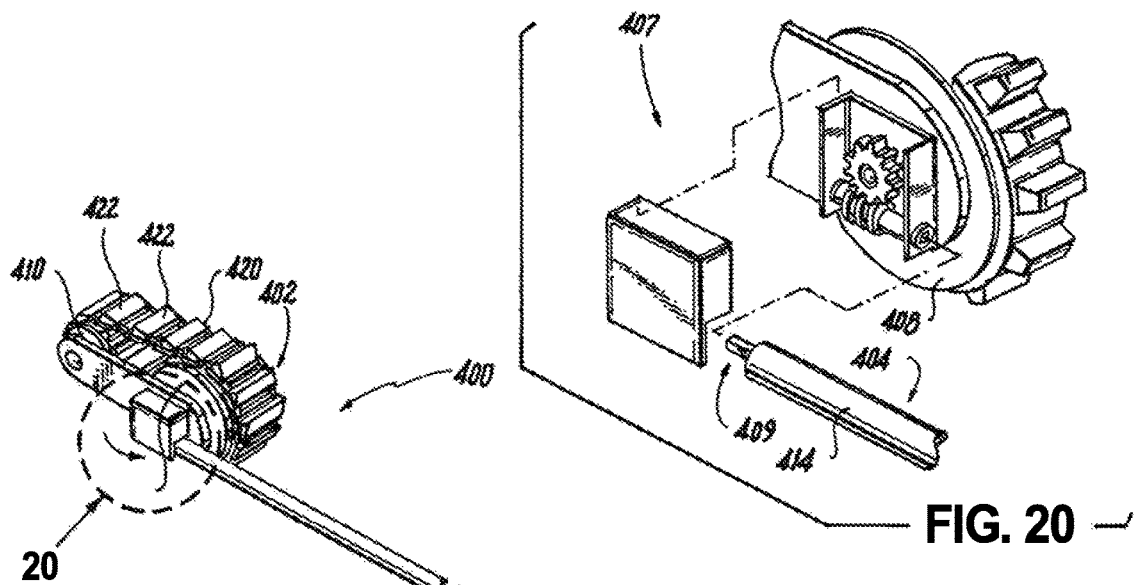
FIG. 19
FIG. 20
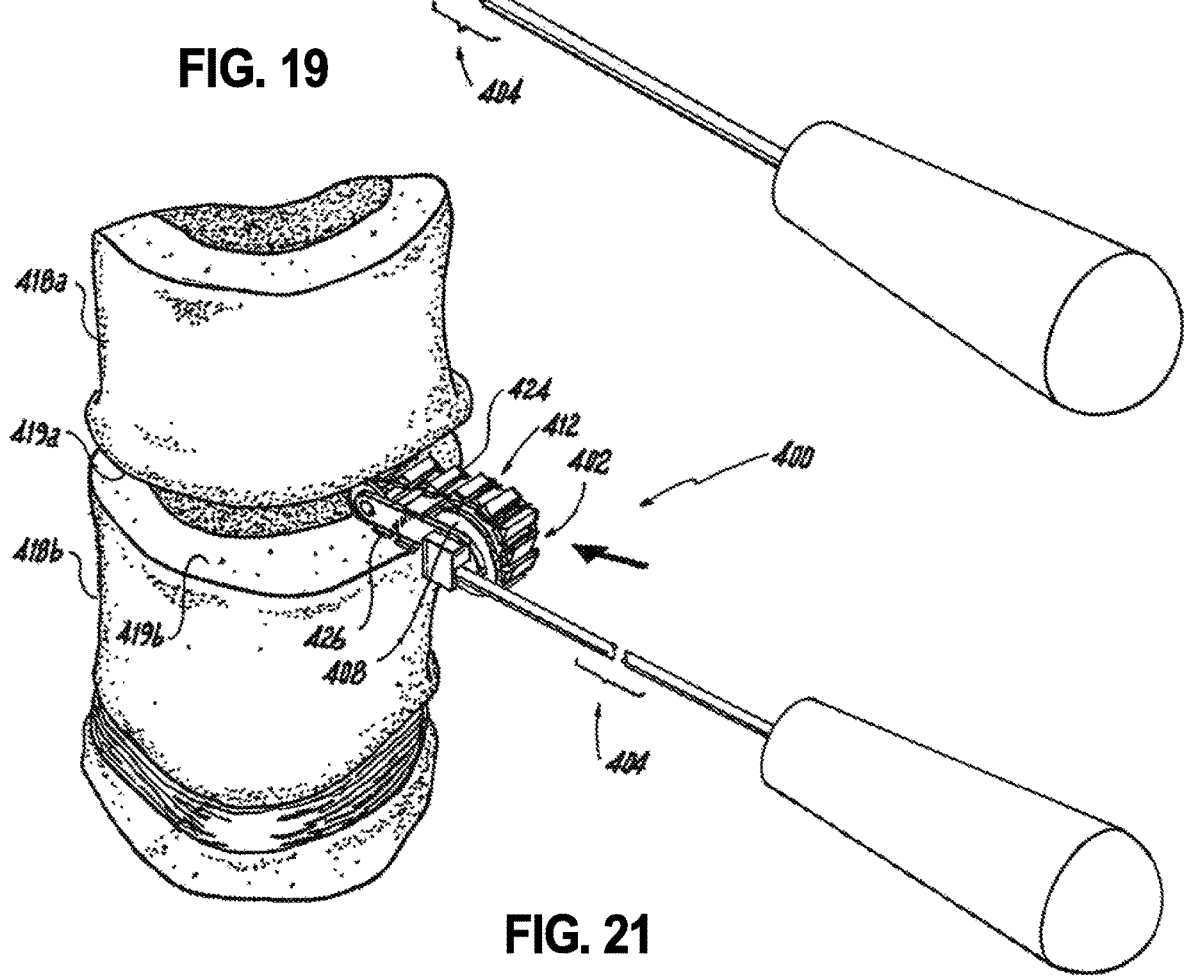
FIG. 21

TRANSLATIONAL INSTRUMENTATION FOR SPONDYLOLISTHESIS AND SCOLIOSIS REDUCTION

CROSS-REFERENCE TO RELATED APPLICATIONS

This application is a divisional of U.S. patent application Ser. No. 15/362,165, filed on Nov. 28, 2016, which is a continuation in part of U.S. patent application Ser. No. 14/569,218, filed Dec. 12, 2014. U.S. patent application Ser. No. 14/569,218, filed Dec. 12, 2014, is a divisional application of U.S. patent application Ser. No. 13/287,811, filed on Nov. 2, 2011 (U.S. Pat. No. 8,936,599). The contents of each above referenced application are incorporated by reference herein in their entirety.

BACKGROUND OF THE INVENTION

1. Field of the Invention

The present invention relates to instruments and methods of treating spinal conditions, and more particularly to instruments and methods for treating spondylolisthesis, scoliosis, and the like.

2. Description of Related Art

Spondylolisthesis is a spinal disorder that arises from two separate conditions. The first involves a lytic defect in the pars interarticularis, otherwise known as a spondylolysis. The lytic condition most commonly occurs where the lumbar spine meets the sacrum, e.g., at L5-S1. The second condition involves a slippage of the vertebra related to degenerated disc disease and facet arthrosis. The degenerative condition usually involves L4-5 segments. However, spondylolisthesis can occur at any level in the lumbar and less commonly in the cervical spine. Treatment of spondylolisthesis often involves a fusion of the two vertebra involved. Motion sparing technologies, such as total disc replacements, are also used to treat milder cases of degenerative spondylolisthesis.

Spondylolisthesis treatment options routinely include spinal fusion procedures. These can be performed with a combined anterior and posterior approach. The anterior approach is performed via a direct anterior transperitoneal or retroperitoneal approach or lateral approach. This surgery allows direct removal of the majority of the disc, and placement of structural grafts in the disc space. Graft materials include autogenous bone from the iliac crest, allograft, and bone morphogenic protein. The discectomy procedure allows a mobility of the motion segment and enhances fusion rates. This is because anterior grafts are placed under compression as compared to posterior fusion masses, which are under tension. The broad surface area between the endplates allow for higher fusion rates.

The distraction of the collapsed disc space of the listhetic segment allows a mild reduction of the listhesis. This reduction is enhanced by impacting a lordotically shaped graft within the intervertebral space. Alternatively, motion sparing technologies have been used for this problem. Posterior reduction techniques using pedicle screw and rod systems have a significant risk of nerve root traction injuries. None of the traditional instruments, including instruments used in anterior approaches, allow for a combination of both distraction of the disc space and correction of listhesis.

Such conventional methods and systems have generally been considered satisfactory for their intended purpose. However, there is still a need in the art for instrumentation to allow for a combination of distraction of the disc space and correction of the listhesis. There also remains a need in the art for such instrumentation that can be used from anterior and other approaches. The present invention provides a solution for these problems.

SUMMARY OF THE INVENTION

The subject invention is directed to a new and useful instrument for spinal procedures, such as for treating spondylolisthesis, scoliosis, and the like. The instrument is a vertebral endplate spreader device having a vertebral endplate spreader and a driver handle. The vertebral endplate spreader includes a linkage with a drive sprocket operatively connected for rotation relative thereto and with a secondary sprocket. The secondary sprocket is operatively connected for rotation relative to the linkage. The vertebral endplate spreader includes a belt operatively connected to the drive sprocket and the secondary sprocket to be driven about a belt axis. The driver handle has a distal end and a proximal end. The distal end is operatively connected to the drive sprocket to actuate rotation of the belt.

In accordance with certain embodiments, the drive sprocket and the secondary sprocket have different diameters to facilitate distraction between respective endplates of two vertebrae. The diameter of the drive sprocket can be larger than the diameter of the secondary sprocket. The belt can include an outer textured surface to engage respective endplates of vertebrae for distraction and correction of vertebral alignment. The outer textured surface can include teeth pointed in a clockwise direction and/or in a counter-clockwise direction with respect to a side of the drive sprocket from which the driver handle extends.

The vertebral endplate spreader can include a gear transmission operatively connected between the drive sprocket and the distal end of the driver handle to reduce a required torque input through the driver handle. The spreader can include a worm gear and worm shaft operatively connected to the drive sprocket to rotate the drive sprocket when driven by the worm shaft. The worm shaft can be a portion of the distal end of the driver handle.

A kit for performing spinal distraction and vertebral alignment includes a vertebral endplate spreader, a driver handle, and a plurality of implants of varying sizes. The kit can include additional vertebral endplate spreaders and additional driver handles of varying sizes. The kit can also include bendable screws of varying sizes for use in one or more of the plurality of implants.

A method of correcting vertebral alignment includes engaging a top surface of a belt of a vertebral endplate spreader to a first vertebra. The method includes engaging a bottom surface of the belt of the vertebral endplate spreader to a second vertebra proximate to the first vertebra. The method includes distracting the first and second vertebrae from one another and translating the vertebrae laterally for correction of alignment of the first and second vertebrae. The distraction and translation are achieved by rotating the belt to move top and bottom surfaces of the belt in opposite directions from one another.

It is contemplated that engaging top and bottom surfaces of the belt to the vertebrae can include approaching the vertebrae with the vertebral endplate spreader from an anterior approach. Translating can include moving the superior of the two vertebrae in a posterior direction to correct a listhesis condition of the vertebrae. Translating can include moving the superior of the two vertebrae in an anterior direction to correct a retrolisthesis condition of the vertebrae. Engaging top and bottom surfaces of the belt to the vertebrae can include approaching the vertebrae with the vertebral endplate spreader from a lateral approach. Translating can include moving the two vertebrae relative to one another in a lateral direction to correct a lateral slippage condition of the vertebrae related to scoliosis.

The method can include inserting an implant between the first and second vertebrae, wherein the implant includes a bore therethrough having a bore entrance defined along a first axis and a bore exit defining a second axis that is angled with respect to the first axis to facilitate implantation of the implant. The method can include securing the implant to the respective endplates of the first and second vertebrae with a flexible screw for passing into the bore of the implant along the first axis and out of the bore of the implant along the second axis.

These and other features of the systems and methods of the subject invention will become more readily apparent to those skilled in the art from the following detailed description of the preferred embodiments taken in conjunction with the drawings.

BRIEF DESCRIPTION OF THE DRAWINGS

So that those skilled in the art to which the subject invention appertains will readily understand how to make and use the devices and methods of the subject invention without undue experimentation, preferred embodiments thereof will be described in detail herein below with reference to certain figures, wherein:

FIG. 1 is a side elevation view of an exemplary embodiment of an instrument constructed in accordance with the present invention, showing the vertebral endplate spreaders mounted to the distal end of a hand operable mechanism for manipulating the spreaders between distracted and retracted positions, and also showing the driver tool for actuating lateral movement of the distal sections of the upper and lower spreaders;

FIG. 2 is a plan view of the instrument of FIG. 1 without the driver, showing the engagement of the spreaders to the hand operable mechanism;

FIG. 3 is an exploded perspective view of the spreaders and driver of FIG. 1, showing the tongs for engaging upper and lower vertebrae;

FIG. 8 is a side elevation view of the instrument of FIG. 1, showing the upper and lower spreaders of the instrument distracting the listhetic vertebrae;

FIG. 9 is a side elevation view of the instrument of FIG. 1, showing the upper and lower spreaders laterally translated relative to one another for correction of the listhesis.

FIG. 10 is a perspective view of another exemplary embodiment of an instrument constructed in accordance with the present invention, showing a vertebral endplate spreader with a belt mounted to the distal end of a driver tool;

FIG. 11 is an exploded perspective of the instrument of FIG. 10, showing the teeth of the belt;

FIG. 12 is a perspective view of another embodiment of an instrument constructed in accordance with the present invention, showing a gear transmission;

FIG. 19 is a perspective view of another exemplary embodiment of an instrument constructed in accordance with the present invention, showing a vertebral endplate spreader with a belt mounted to the distal end of a driver tool;

FIG. 20 is an exploded perspective of a portion of the instrument of FIG. 19, showing the worm gear interface between the driver handle and the drive sprocket;

FIG. 21 is a perspective view of the instrument of FIG. 19, showing the instrument being introduced from anterior approach to a listhetic pair of lumbar vertebrae;

DETAILED DESCRIPTION OF THE PREFERRED EMBODIMENTS

Figure 4:
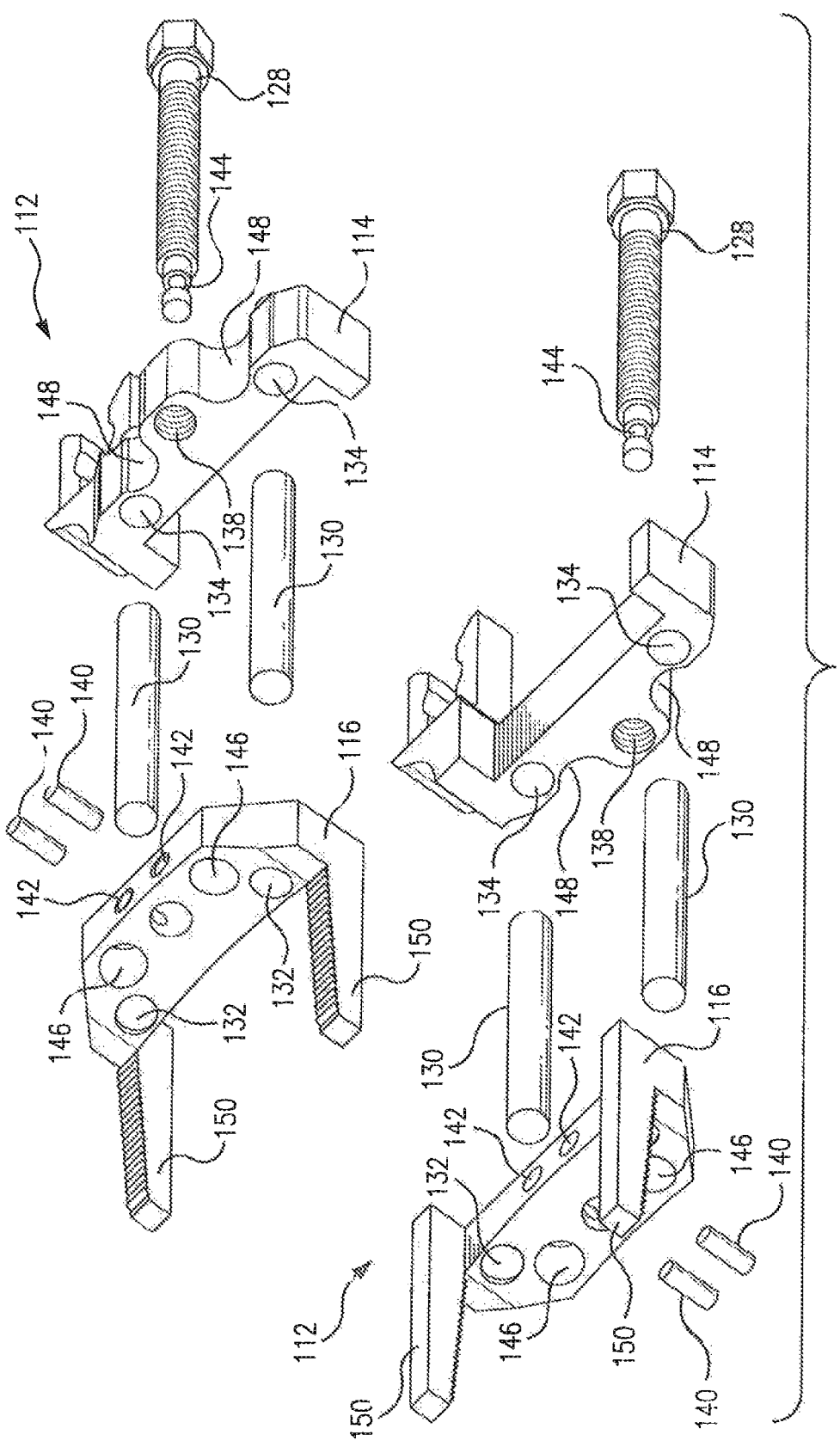
FIG. 4 is an exploded perspective view of the upper and lower spreaders of FIG. 3, showing the separate proximal and distal sections of the each spreader as viewed from above.

Reference will now be made to the drawings wherein like reference numerals identify similar structural features or aspects of the subject invention. For purposes of explanation and illustration, and not limitation, a partial view of an exemplary embodiment of an instrument in accordance with the invention is shown in FIG. 1 and is designated generally by reference character 100. Other embodiments of instruments in accordance with the invention, or aspects thereof, are provided in FIGS. 2-24, as will be described. The system of the invention can be used to treat spondylolisthesis, scoliosis, and the like.

Instrument 100 includes a distraction mechanism 102 having a proximal end 104 and an opposed distal end 106. Distal end 106 includes opposed first and second end members 108 and 110, respectively. A first vertebral endplate spreader 112 includes a proximal spreader section 114. Proximal spreader section 114 is mounted to first end member 108 of distraction mechanism 102 by mounting pin 122 shown in FIG. 2. First spreader 112 also includes a distal spreader section 116 operatively connected to proximal spreader section 114 for lateral movement relative to proximal spreader section 114. A second vertebral endplate spreader 118 is mounted to second end member 110 of distraction mechanism 102 by mounting pin 124, which is identified in FIG. 1. The first and second spreaders 112 and 118 are each configured to engage a respective vertebra for correction of vertebral alignment as will be described in greater detail below.

Distraction mechanism 102 is configured and adapted to distract the spreaders 112 and 118 apart from one another and to retract the spreaders 112 and 118 together along a distraction axis A responsive to action imparted on proximal end 104 of distraction mechanism 102. For example, if a user squeezes the handles of proximal end 104, spreaders 112 and 118 will be distracted apart from one another, and if a user allows the handles of proximal end 104 to move apart, for example by action of spring 120, spreaders 112 and 118 will be retracted towards one another.

Referring now to FIG. 3, in addition to being able to move together and apart along distraction axis A, spreaders 112 and 118 can also move laterally with respect to one another, i.e., in a lateral direction relative to distraction axis A. This lateral movement is made possible by the fact that the spreaders 112 and 118 are each split into proximal and distal sections 114 and 116 to vary the offset as needed by the preexisting listhesis. Driver 126 is used to turn actuator screws 128 to actuate the displacement of distal spreader sections 116 relative to proximal spreader sections 114.

Lateral actuation of spreaders 112 and 118 is further described with reference to FIG. 4, which shows parts of spreaders 112 and 118 separated and in the orientation of the procedures described below with reference to FIGS. 5-9. A pair of guides 130 is provided for each spreader 112 and 118, engaged with the proximal and distal spreader sections 114 and 116 to maintain a parallel relationship between the proximal and distal spreader sections 114 and 116 during relative lateral travel thereof. Guides 130 are rigidly mounted in bores 132 of distal spreader sections 116 and are slideably engaged in bores 134 of proximal spreader sections 114.

A linear actuator is provided in each spreader 112 and 118 in the form of actuator screw 128, the threads of which engage with corresponding threads in bore 138 of the respective proximal spreader section 114. Each actuator screw 128 is rotatably engaged to a respective distal spreader section 116, with actuator pins 140 mounted in bores 142 and engaged with groove 144 of each respective actuator screw 128. Rotation of actuator screw 128 adjusts separation of the proximal and distal spreader sections 114 and 116 for relative lateral travel thereof.

Each distal spreader section 116 includes two bone screw bores 146 to provide passages for bone screws to affix each distal spreader section 112 to a respective vertebra. Proximal spreader sections 114 includes bone screw grooves 148 to provide passage for bone screws and any suitable driver device for affixing distal spreader sections 112 to respective vertebra. Each of the distal spreader sections 116 includes a pair of tongs 150 for engaging opposed vertebral endplates for distraction of opposed vertebrae, as described in greater detail below.

Figure 5:
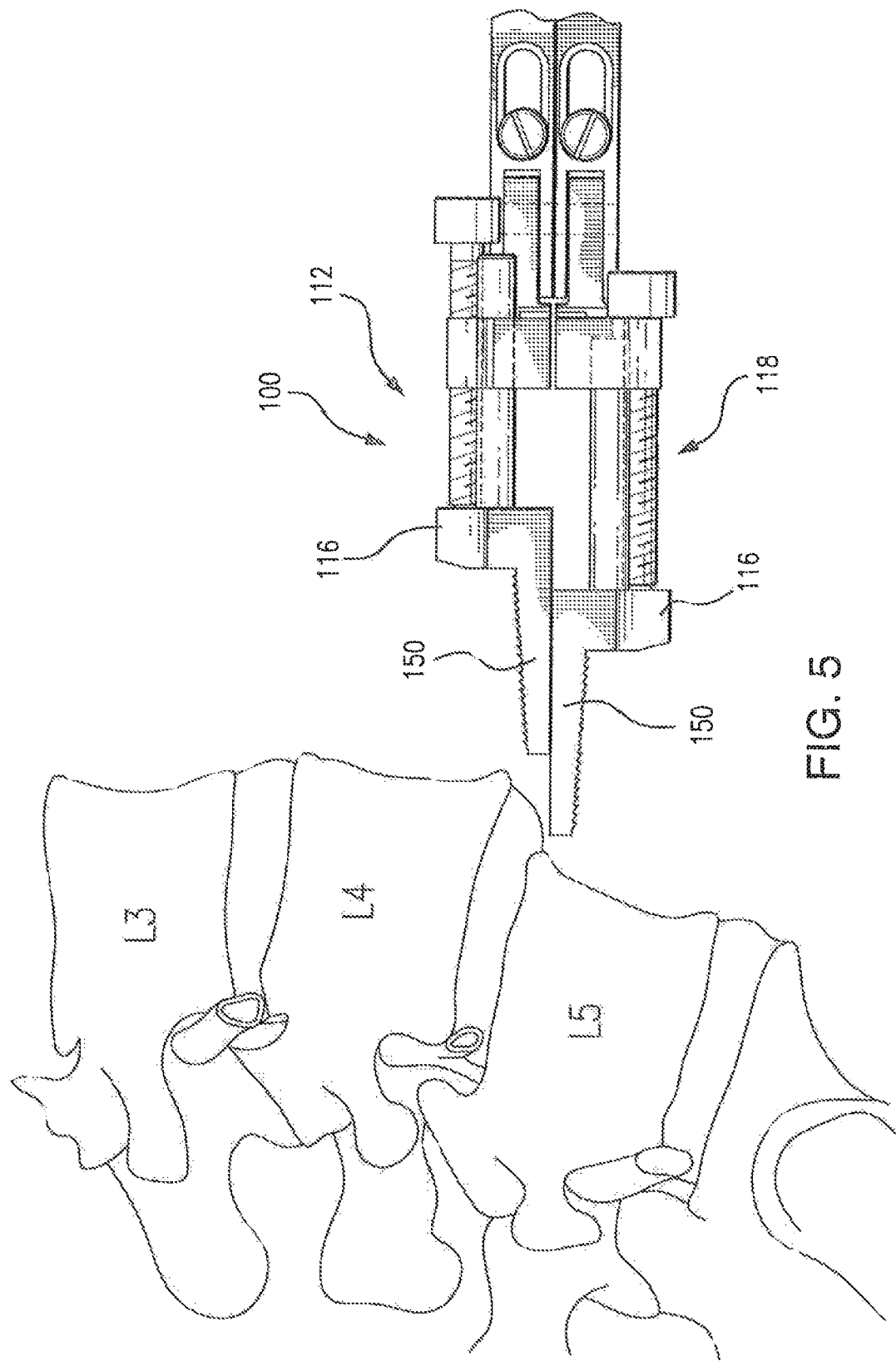
FIG. 5 is a side elevation view of the instrument of FIG. 1, showing the instrument being introduced from an anterior approach to a listhetic pair of lumbar vertebrae.
Figure 6:
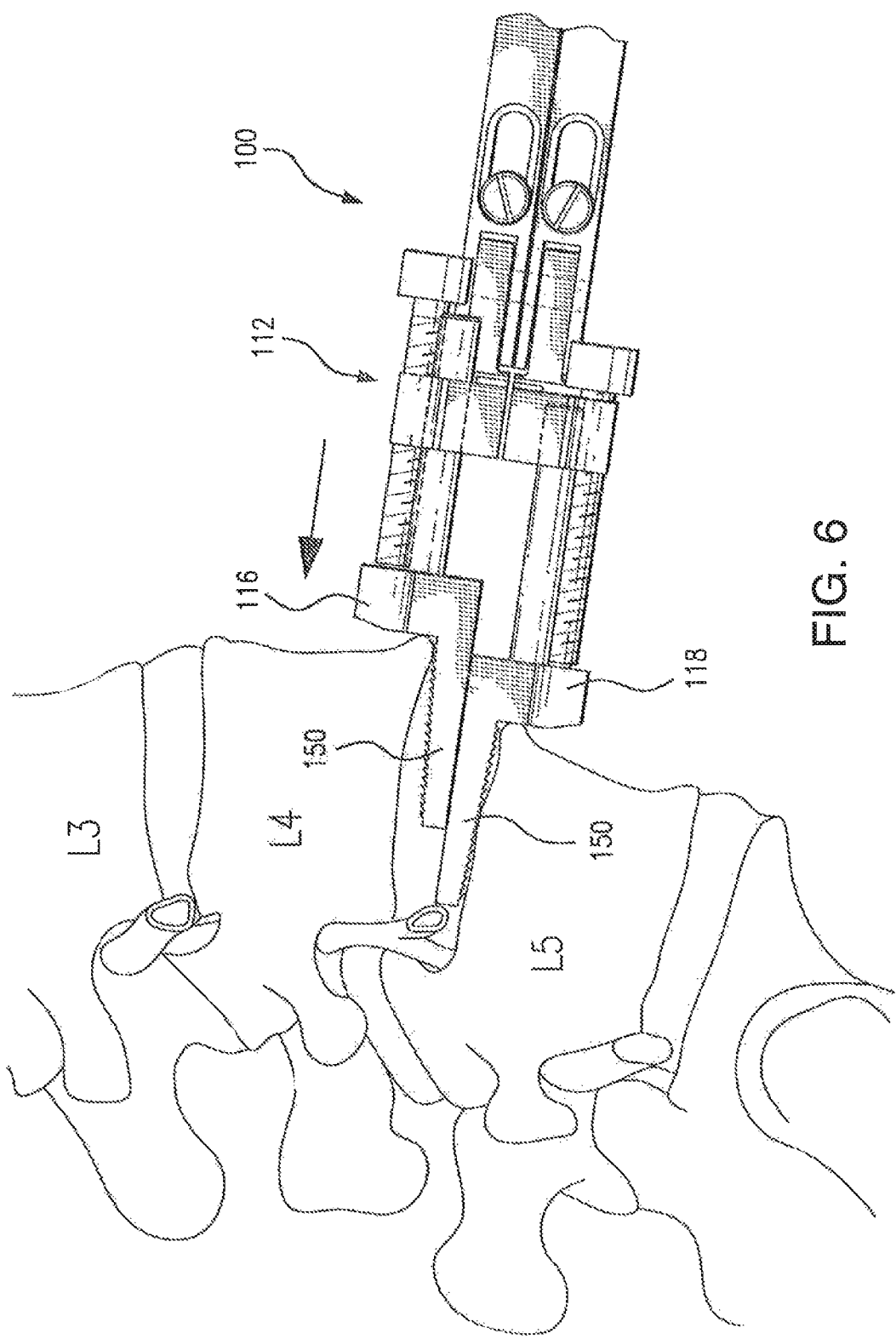
FIG. 6 is a side elevation view of the instrument of FIG. 1, showing the tongs of the instrument being positioned between the listhetic vertebrae.

Referring now to FIGS. 5-9, exemplary methods are described of using instrument 100 for correction of vertebral alignment. FIG. 5 schematically shows instrument 100 approaching listhetic vertebrae L4 and L5 from an anterior approach. The upper or first spreader 112 has its distal spreader section 116 with corresponding tongs 150 in a retracted position. The lower or second spreader 118 has its distal spreader section 116 and corresponding tongs in an advanced position. The relative positions of the upper and lower distal spreader sections 116 corresponds to the offset in alignment of the L4 and L5 vertebrae. As indicated in FIG. 6, tongs 150 of distal spreader section 116 of first spreader 112 are engaged to the listhetic endplate of the L4 vertebra, i.e., the superior or cephalad of the two listhetic vertebrae, and prongs 150 of second spreader 118 are engaged to the adjacent endplate of the L5 vertebra, i.e., the inferior or caudal vertebra.

Figure 7:
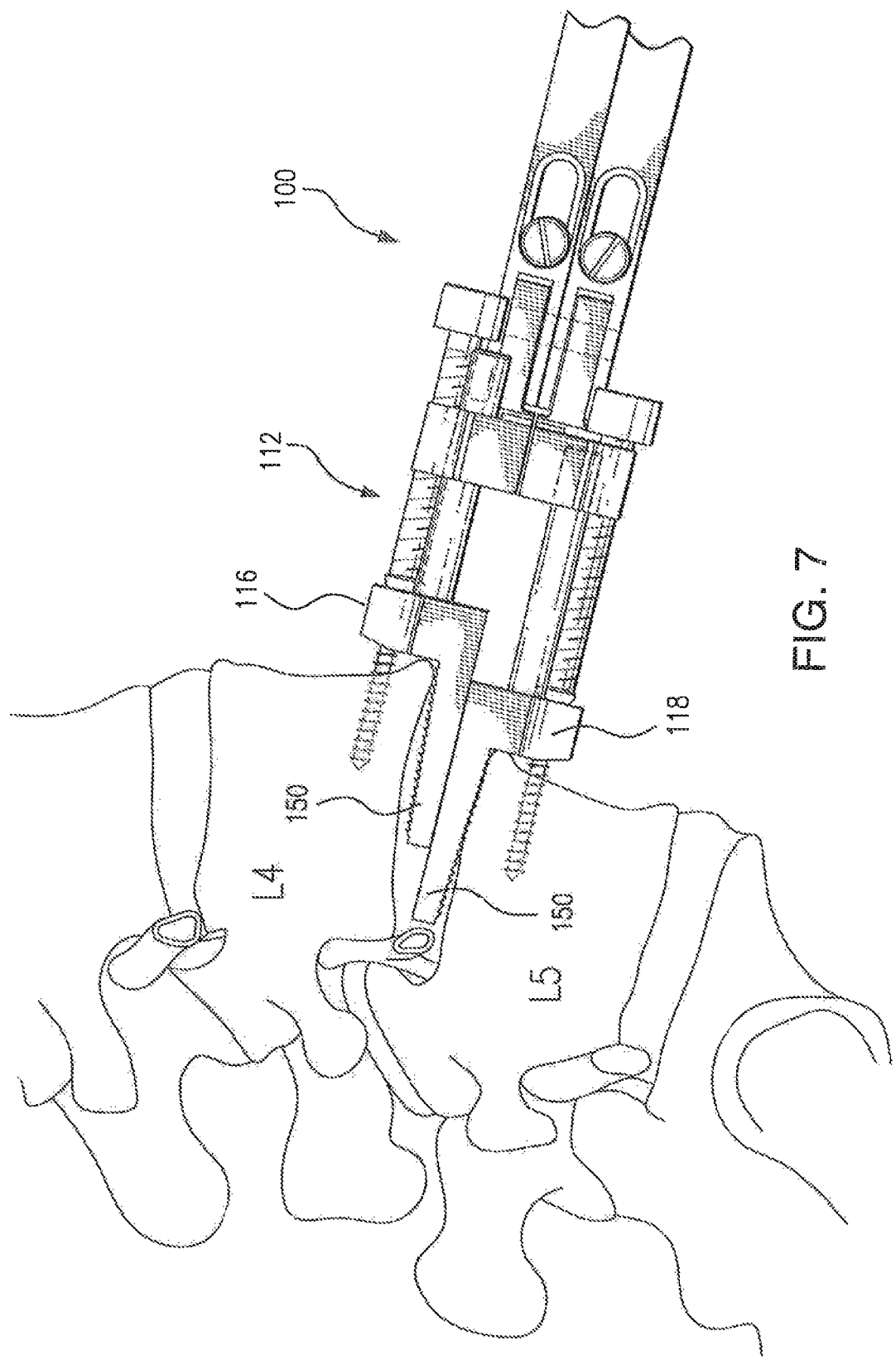
FIG. 7 is a side elevation view of the instrument of FIG. 1, showing the upper and lower spreaders of the instrument mounted to the respective vertebrae.

With instrument 100 engaged with the listhetic vertebrae as shown in FIG. 6, the vertebrae can be distracted apart as shown in FIGS. 8 and 9. FIG. 7 shows bone screws affixing the first and second spreaders 112 and 118 to the respective vertebrae prior to distraction. Those skilled in the art will readily appreciate that one or both spreaders 112 and 118 can be affixed with bone screws before or after distraction without departing from the spirit and scope of the invention. Moreover, bone screw affixation may be omitted for one or both of the spreaders 112 and 118, for example if the forces engaging the respective prongs 150 to the vertebrae provide sufficient fixation without bone screws. Having both spreaders 112 and 118 secured with screws to the respective vertebrae provides extra stability.

With the spreaders 112 and 118 affixed to the respective vertebrae as shown in FIG. 7, the proximal end 104 of distraction mechanism 102 can be actuated to distract the vertebrae along distraction axis A as indicated by the heavy arrows in FIG. 8. With the listhetic vertebrae L4 and L5 distracted, a corpectomy, discectomy, or the like can be performed as needed.

Referring now to FIG. 9, direct posterior translational force is applied after a thorough discectomy and distraction has been performed. In order to correct the listhesis, driver 126 is engaged with actuator screw 128 up upper spreader 112 and turned to spread the upper proximal and distal spreader sections 114 and 116 apart. The actuator screw 128 on lower spreader 118 can also be turned to move the lower distal spreader section 116 in the opposite direction. This action translates the distal spreader sections 116 relative to the proximal spreader sections 114 laterally with respect to distraction axis A for correction of alignment of the L4 and L5 vertebrae. The action of driver 126 and distal spreader sections 116 are indicted by the heavy arrows of FIG. 9. Universal joint 152 accommodates a range of angles of approach for driver 126 for ease of application. Driver 126 is depicted with a female hex head, which those skilled in the art will readily appreciate is exemplary, as any suitable driver/head type or linear actuator type can be used without departing from the spirit and scope of the invention.

During an operation as described above, the surgeon can decide whether a complete or partial reduction of the listhesis should be attempted. After adequate reduction has been achieved, an interbody graft or motion sparing device can be placed through the enhanced slot between the superior and inferior distractor tongs 150. The surgeon can check by direct visualization or intra-operative x-rays as to the vertebral alignment and placement of the interbody graft(s) or motion sparing device. If a fusion is performed, instrument 100 is then removed, including the anterior screws. Supplemental anterior plate fixation can then be applied using the holes previously made in the vertebrae to affix the spreaders 112 and 118. The bores 134 in spreader 112 and corresponding bores 134 in spreader 118 are spaced apart to allow for a corresponding anterior plating system after the reduction has been performed.

Instrument 100 will thus allow a correction of vertebral alignment related to spondylolisthesis. The systems and methods described herein can also be applied for a retrolisthesis, which is a much less common spinal condition. In this case, the lateral motion of distal spreader sections 116 is reversed to be anterior rather than posterior. Furthermore, it is also contemplated that a smaller version of instrument 100 can be used for other applications where smaller size is needed, for example in use on the cervical spine.

In the orientation shown in FIGS. 5-9, first spreader 112 may be referred to as the upper, superior, or cephalad spreader, and second spreader 118 may be referred to as the lower, inferior, or caudal spreader. Those skilled in the art will readily appreciate that while each of the spreaders 112 and 118 is shown and described as split into proximal and distal sections 116 and 114 for lateral movement, it is also possible to use only one split spreader with another spreader that is not split without departing from the spirit and scope of the invention. If both spreaders are split as described above, additional lateral travel is possible compared to embodiments having only one spreader that is split.

As shown in FIGS. 10 and 11, another embodiment of an instrument for spinal procedures, such as for treating spondylolisthesis, scoliosis, and the like, is a vertebral endplate spreader device 200 having a vertebral endplate spreader 202 and a driver handle 204. Vertebral endplate spreader 202 includes a linkage 206 with a drive sprocket 208 operatively connected for rotation relative to linkage 206 and with a secondary sprocket 210. Secondary sprocket 210 is operatively connected for rotation relative to linkage 206. Vertebral endplate spreader 202 includes a belt 212 operatively connected to drive sprocket 208 and secondary sprocket 210 to be driven about a belt axis B. Driver handle 204 has a distal end 214 and a proximal end 216. Distal end 214 is operatively connected to drive sprocket 208 to actuate rotation of belt 212.

With reference now to FIG. 12, another embodiment of a vertebral endplate spreader 302 includes a gear transmission 322 operatively connected between drive sprocket 308 and distal end 314 of driver handle 304 to reduce the required torque input through driver handle 304, making the rotation of drive sprocket 308 easier for the user.

Figure 13:
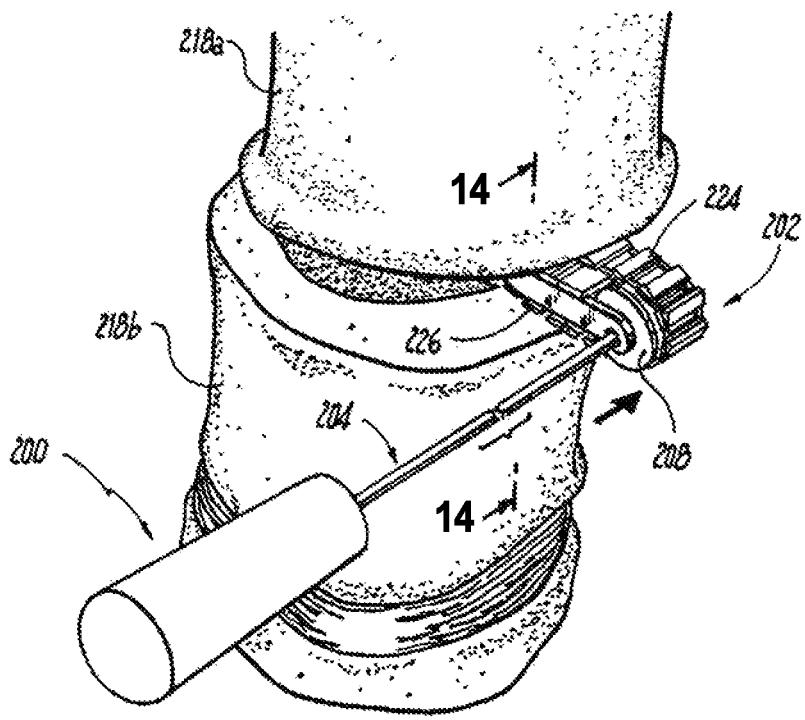
FIG. 13 is a perspective view of the instrument of FIG. 10, showing the instrument being introduced from a lateral approach to a listhetic pair of lumbar vertebrae and the vertebral endplate spreader being positioned between the listhetic pair of vertebrae.
Figure 14:
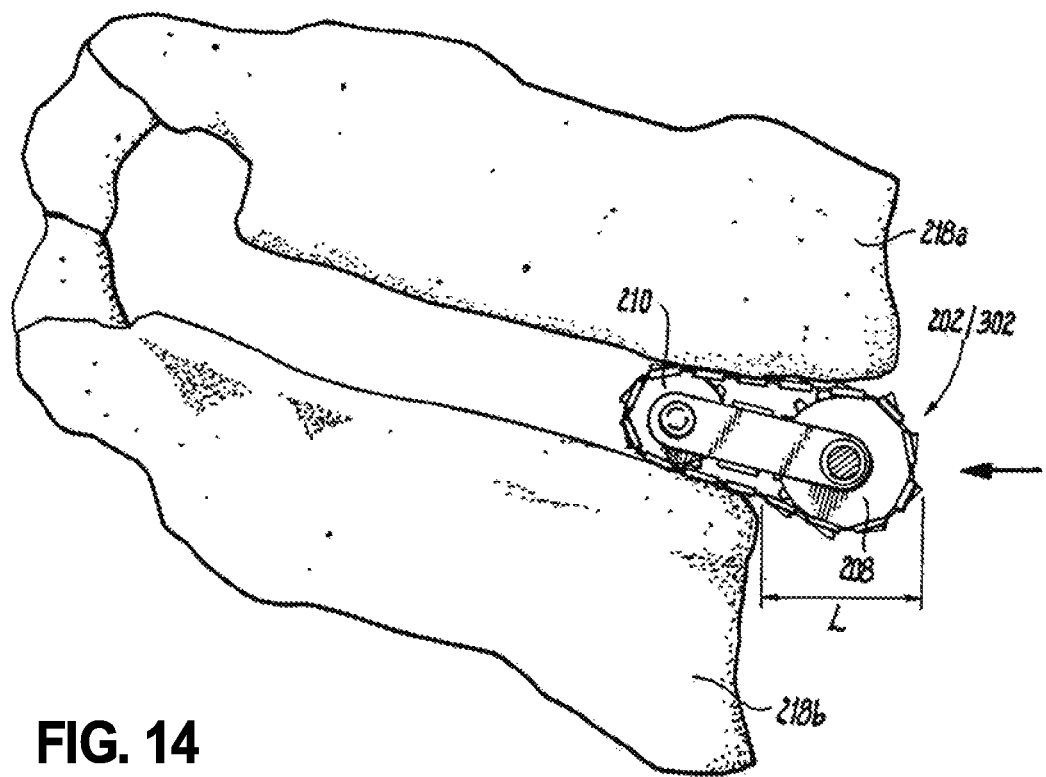
FIG. 14 is a side elevation view of a portion of the instrument of FIG. 10, showing the position of the vertebral endplate spreader between the listhetic vertebrae.

As shown in FIGS. 13 and 14, drive sprocket 208 and secondary sprocket 210 have different diameters to facilitate distraction between respective endplates of two vertebrae 218a and 218b. For example, diameter of drive sprocket 208 can be larger than the diameter of secondary sprocket 210. The smaller diameter of secondary sprocket 210 permits easier and less traumatic placement of spreader 202, while the larger diameter of drive sprocket 208 facilitates distraction as belt 212 is rotated.

With continued reference to FIGS. 13 and 14, correcting vertebral alignment includes engaging a top surface 224 of belt 212 to a first vertebra 218a, and engaging a bottom surface 226 of belt 212 of vertebral endplate spreader 202 to a second vertebra 218b proximate to first vertebra 218a. First and second vertebrae, 218a and 218b, respectively, are separated by a distance L in a listhetic position. While vertebral endplate spreader 202 engages top and bottom surfaces 224 and 226, respectively, of belt 212 with vertebrae 218a and 218b from a lateral approach, those skilled in the art will readily appreciate that device 200 can be used to insert vertebral endplate spreader 202 from a posterior or anterior direction.

Figure 15:
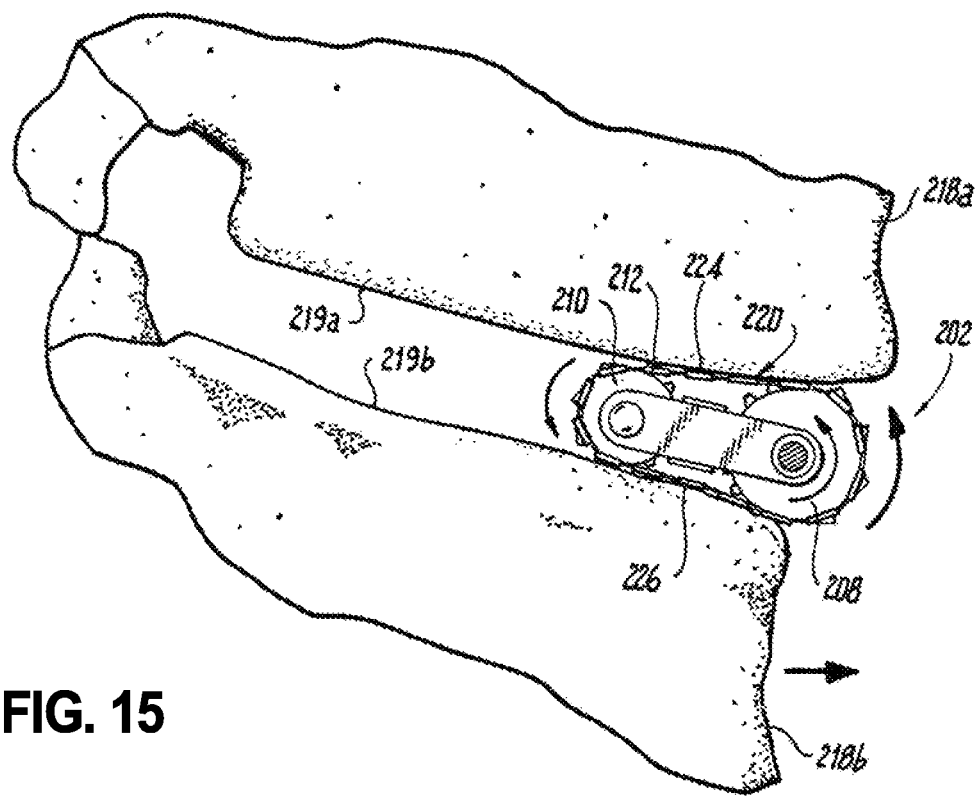
FIG. 15 is a side elevation view of the instrument of FIG. 10, showing the position of the vertebral endplate spreader between the listhetic vertebrae as the sprocket is rotated counter clock-wise.

Now with reference to FIG. 15, belt 212 includes an outer textured surface 220 to engage respective endplates 219a and 219b of vertebrae 218a and 218b for distraction and correction of vertebral alignment. Outer textured surface 220 includes teeth 222 pointed in a counter-clockwise direction with respect to a side of drive sprocket 208 from which driver handle 204 extends. Those skilled in the art will readily appreciate that teeth 222 can be pointed clockwise and/or can be neutral, e.g. neither clockwise nor counter-clockwise.

With continued reference to FIG. 15, rotating drive sprocket 208 rotates belt 212, as indicated schematically by the counter-clockwise arrows. Rotation of belt 212 moves top and bottom surfaces 224 and 226, respectively, of belt 212 in opposite directions from one another distracting first and second vertebrae 218a and 218b, respectively, from one another and translating vertebrae 218a and 218b anteriorly and posteriorly for correction of alignment. Those skilled in the art will readily appreciate that translating includes moving the superior of the two vertebrae, e.g. vertebra 218a, in a posterior direction to correct a listhesis condition of the vertebrae, and/or includes moving the superior of the two vertebrae in an anterior direction to correct a retrolisthesis condition of the vertebrae. It is also contemplated that translating includes moving the two vertebrae relative to one another in a lateral direction to correct a lateral slippage condition of the vertebrae related to scoliosis. This translation in a lateral direction can be achieved by inserting vertebral endplate spreader 202 from an anterior direction or a posterior direction, e.g. ninety degrees from where vertebral endplate spreader 202 is shown in FIGS. 13-15, so that when rotating drive sprocket 208 rotates belt 212 vertebrae 218a and 218b are translated laterally with respect to one another.

Figure 16:
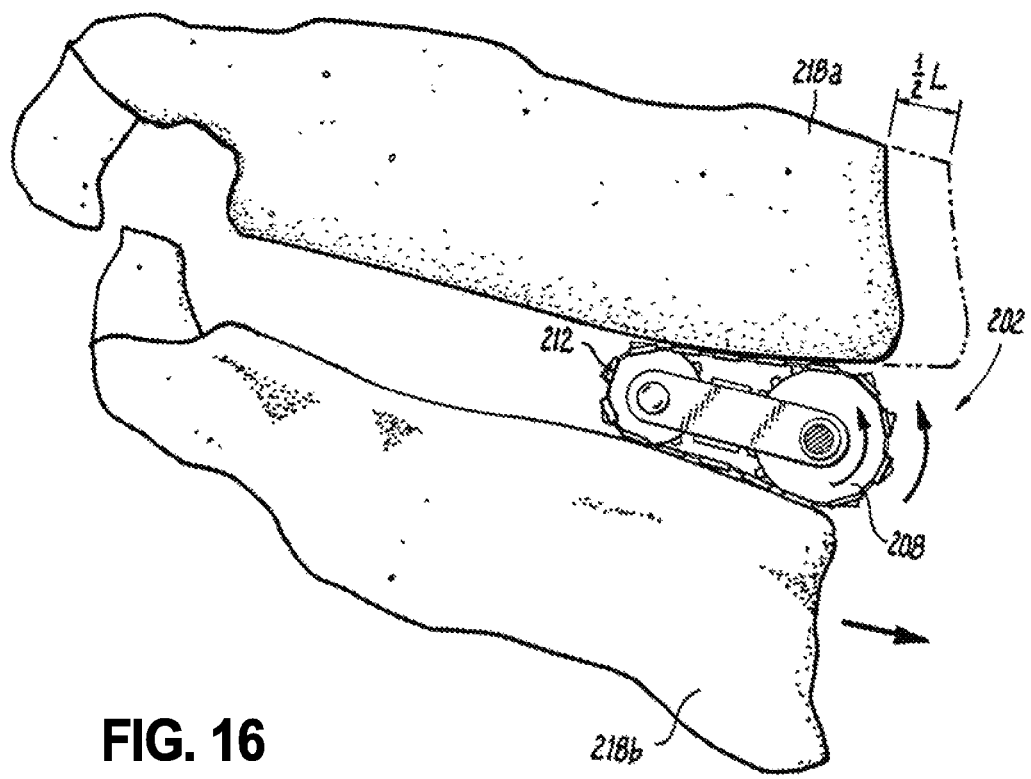
FIG. 16 is a side elevation view of the instrument of FIG. 10, showing the position of the vertebral endplate spreader between the vertebrae in a corrected position.
Figure 17:
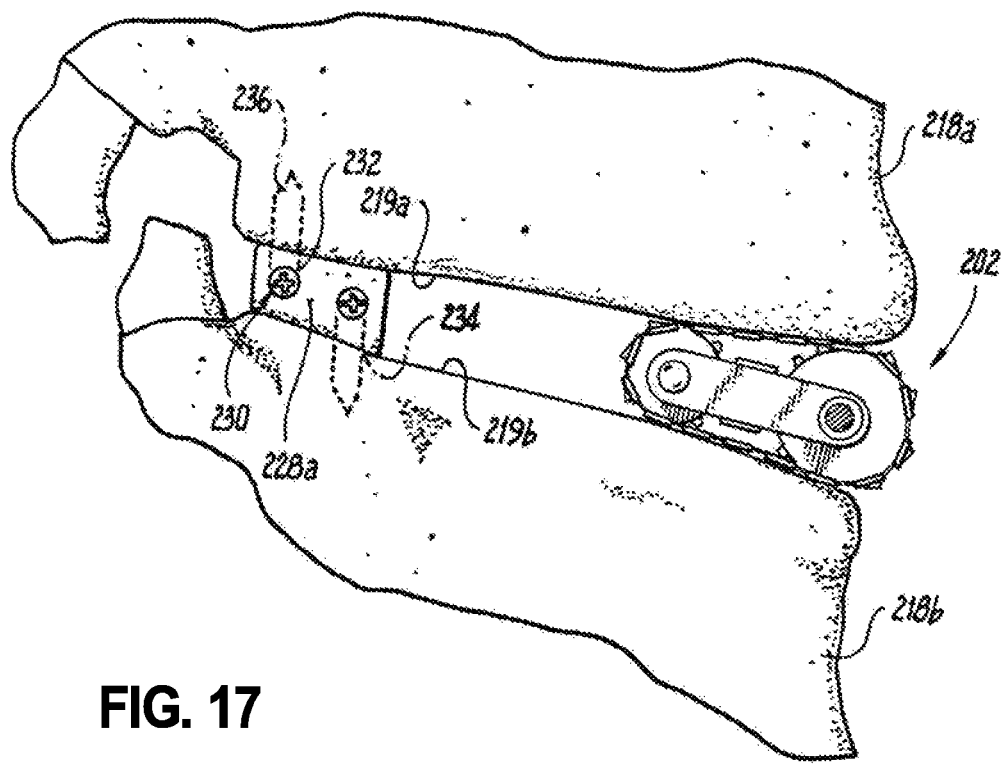
FIG. 17 is a side elevation view of the instrument of FIG. 10, showing the placement of an implant between the corrected vertebrae.
Figure 18:
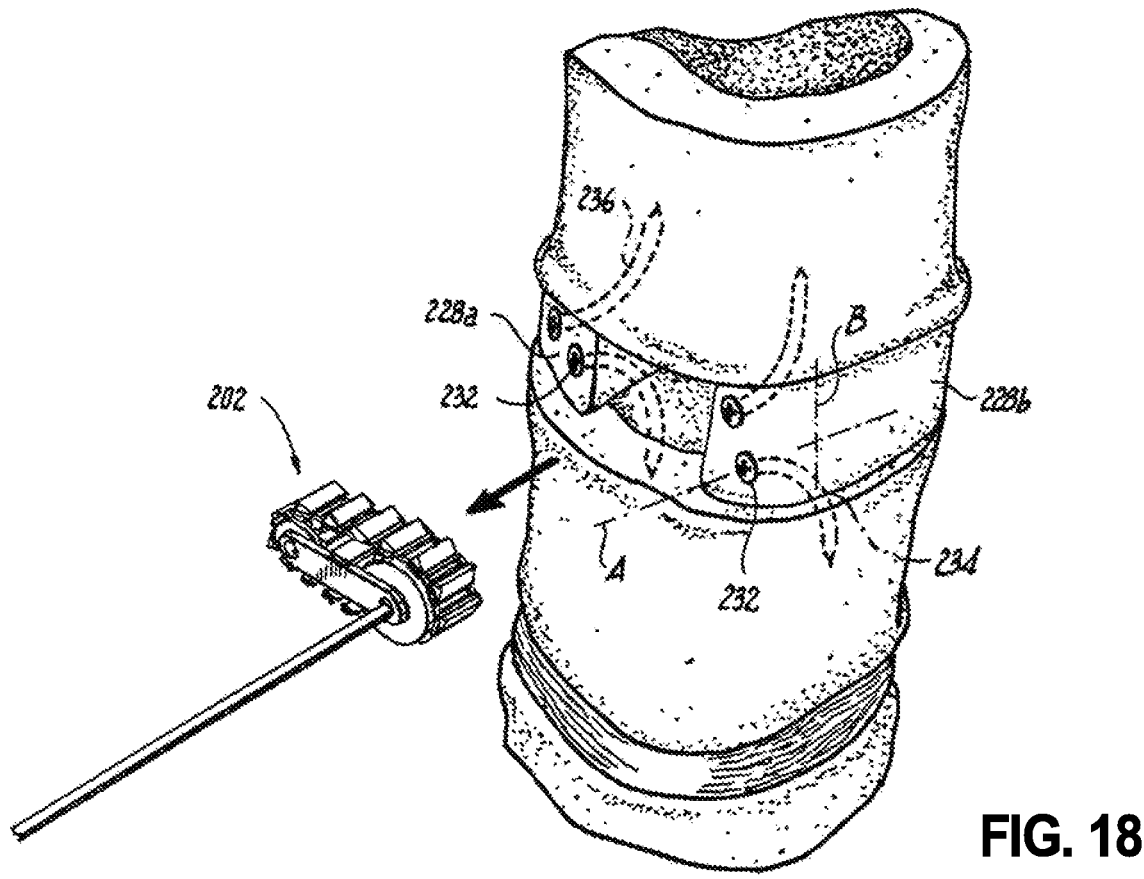
FIG. 18 is a perspective view of the instrument of FIG. 10, showing the removal of the vertebral endplate spreader and the placement of another implant.

As shown in FIGS. 16-18, after translation, vertebrae 218a and 218b are aligned with one another in the posterior to anterior direction. It is contemplated that each vertebra 218a and 218b moves approximately ½L in opposing directions in order to align with another. Once vertebrae 218a and 218b aligned, an implant 228a is inserted between vertebrae 218a and 218b. After insertion of implant 228a, a second implant 228b is inserted. Implant 228b is similar to implant 228a. Each implant 228a and 228b includes bores 230 therethrough. Each bore 230 has a bore entrance 232 defined along a first axis C and a bore exit 234 defining a second axis D that is angled with respect to first axis C to facilitate implantation of implants 228a and 228b. Implants 228a and 228b are secured to the respective endplates 219a and 219b of vertebrae 218a and 218b with flexible screws 236. Flexible screws 236 pass into their respective bore 230 along first axis C and out of their respective bore 230 along second axis D. Once both implants 228a and 228b are inserted and secured, vertebral endplate spreader 202 is removed from the same direction as it was inserted, as indicated schematically by the arrow in FIG. 18.

With reference now to FIGS. 19-20, another embodiment of a vertebral endplate spreader device 400 is shown. Device 400 is similar to device 200. Device 400 includes a vertebral endplate spreader 402 and a driver handle 404. Vertebral endplate spreader 402 includes a worm gear 407 for driving drive sprocket 408 instead of a direct-drive drive sprocket, e.g. drive sprocket 208. Device 400 includes a worm shaft 409 operatively connected to drive sprocket 408 through worm gear 407 to rotate drive sprocket 408 when driven by the worm shaft 409. Worm shaft 409 is shown as portion of a distal end 414 of driver handle 404, however, those skilled in the art will readily appreciate that worm shaft 409 can be separate from, but operatively connected to, driver handle 404.

As shown in FIG. 21, drive sprocket 408 and secondary sprocket 410 are similar to drive sprocket 208 and secondary sprocket 210. Correcting vertebral alignment includes engaging a top surface 424 of a belt 412 of vertebral endplate spreader 402 to a first vertebra 418a, and engaging a bottom surface 426 of belt 412 to a second vertebra 418b proximate to first vertebra 418a. Belt 412 includes teeth 422, similar to teeth 422. While vertebral endplate spreader 402 engages top and bottom surfaces 424 and 426, respectively, of belt 412 with vertebrae 418a and 418b from an anterior approach, those skilled in the art will readily appreciate that device 400 can be used to insert vertebral endplate spreader 402 from a posterior and/or lateral direction.

With reference to FIGS. 20-21, once engaged, drive sprocket 408 is driven by rotation of worm shaft 409 through driver handle 404. Drive sprocket 408 dives belt and secondary sprocket 410 similar to drive sprocket 208. Rotation of belt 412 moves top and bottom surfaces 424 and 426, respectively, of belt 412 in opposite directions from one another distracting first and second vertebrae 418a and 418b, respectively, from one another and translating vertebrae 418a and 418b anteriorly and posteriorly for correction of alignment. It is also contemplated that vertebrae 418a and 418b can be translated in a lateral direction by inserting vertebral endplate spreader 402 from a lateral direction, so that when rotating drive sprocket 408 rotates belt 412 vertebrae 418a and 418b are translated laterally with respect to one another.

Figure 22:
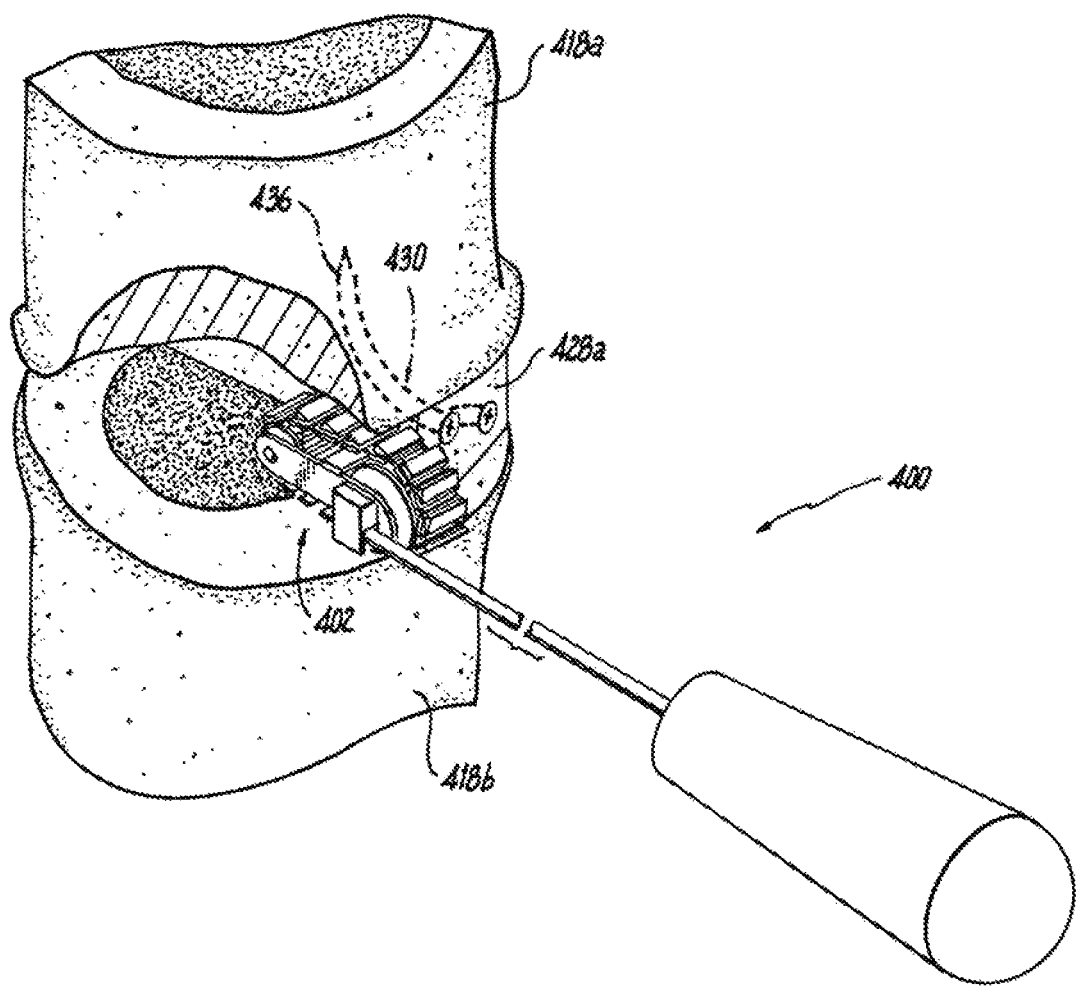
FIG. 22 is a perspective view of the instrument of FIG. 19, showing the vertebral endplate spreader positioned between the vertebrae after correction of the listhesis and showing an implant between the vertebrae.
Figure 23:
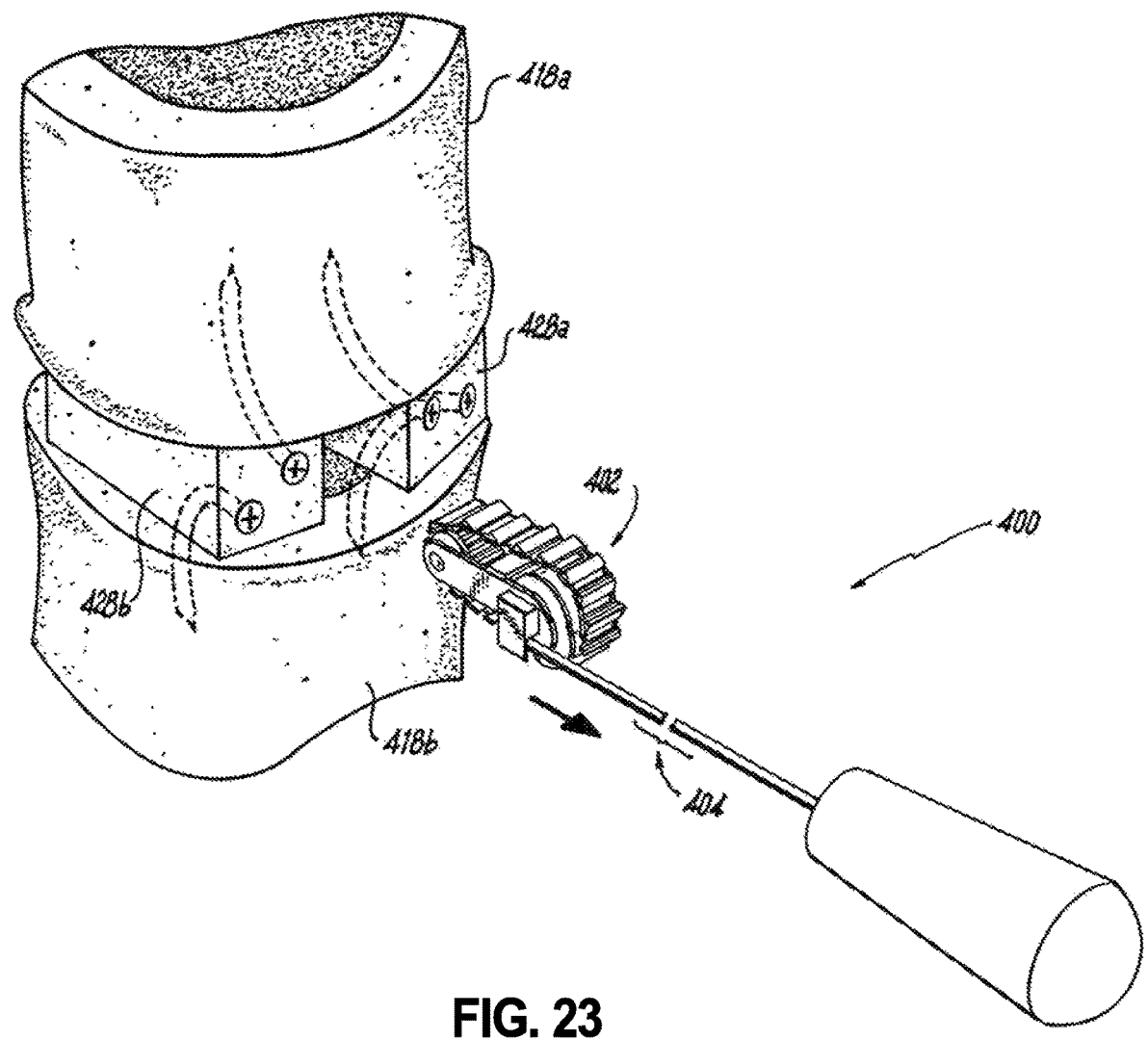
FIG. 23 is a side elevation view of the instrument of FIG. 19, showing the removal of the vertebral endplate spreader and the placement of another implant.

As shown in FIGS. 22-23, after posterior-anterior translation, vertebrae 418a and 418b are aligned with one another. Once vertebrae 418a and 418b aligned, an implant 428a is inserted between vertebrae 418a and 418b. Implant 428a is similar to implant 228a. After insertion of implant 428a, a second implant 428b is inserted. Implant 428b is similar to implant 428a. Once both implants 428a and 428b are inserted and secured, vertebral endplate spreader 402 is removed from the same direction as it was inserted, as indicated schematically by the arrow in FIG. 23.

Figure 24:
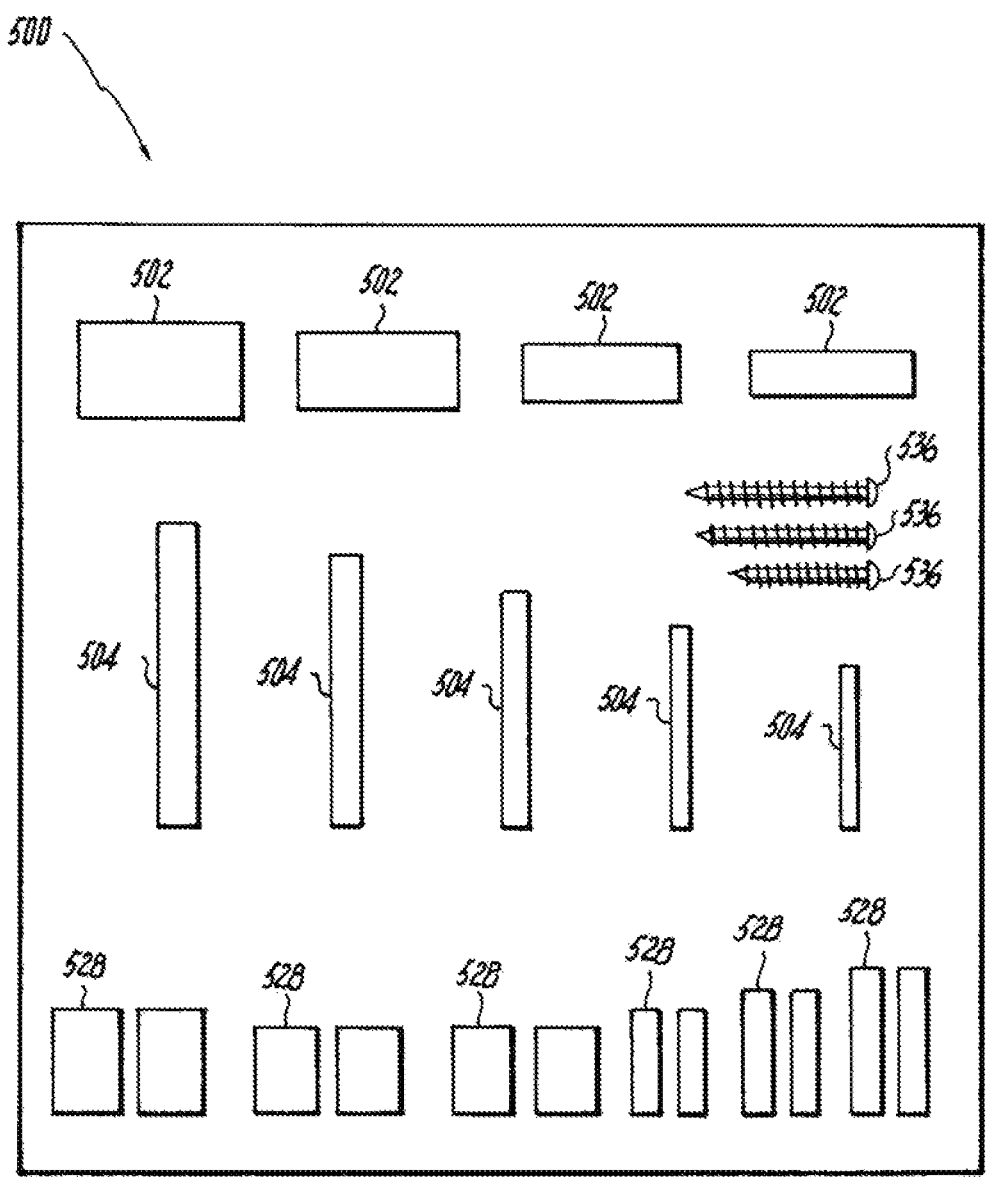
FIG. 24 is a schematic depiction of a kit for performing spinal distraction and vertebral alignment constructed in accordance with an embodiment of the present invention, showing a plurality of driver handles, vertebral spreaders, implants and bendable screws.

With reference now to FIG. 24, a kit 500 for performing spinal distraction and vertebral alignment includes a vertebral endplate spreader 502, similar to vertebral endplate spreaders 202 and 402, a driver handle 504, similar to driver handles 204 and 404 and a plurality of implants 528 of varying sizes, similar to implants 228a, 228b, 428a and 428b. Kit 500 includes additional vertebral endplate spreaders 502 and additional driver handles 504 of varying sizes. Those skilled in the art will readily appreciate that driver handles 504 can also be adjustable in length. Kit 500 also includes bendable screws 536, similar to screws 236 and 436, of varying sizes for use in one or more of implants 528.

While described above in the exemplary context of spondylolisthesis, it is contemplated that other conditions can also be treated using the systems and methods of the invention. For example, there are several forms of scoliosis. These include congenital, idiopathic, and degenerative forms. Deformity of the spine involves a lateral or coronal curvature of the spine. In the lumbar spine, especially in degenerative scoliosis, there is often a lateral slippage of one vertebra relative to another. The instrumentation described above to reduce an anterior spondylolisthesis can be used in a lateral approach on the convexity of the curve to reduce the scoliosis and at the same time allow intervertebral distraction. An instrument adapted from instruments 100, 200 or 400 for treating scoliosis or similar applications can be of a smaller diameter and, in the case of instrument 100, can have one prong on each of the spreaders instead of the two prongs 150 shown and described above.

The methods and instruments described herein advantageously allow for both distraction and relative lateral repositioning of vertebrae. Additional advantages include allowing for disc space distraction which enhances foraminal height. This increased foraminal height reduces the potential for nerve root entrapment during a reduction of the listhesis.

The methods and systems of the present invention, as described above and shown in the drawings, provide for methods and instruments for correcting misalignment of vertebrae with superior properties including distracting and laterally repositioning vertebrae with the same instrument. While the apparatus and methods of the subject invention have been shown and described with reference to preferred embodiments, those skilled in the art will readily appreciate that changes and/or modifications may be made thereto without departing from the spirit and scope of the subject invention.

What is claimed is:

1. A method of correcting vertebral alignment comprising:
engaging a top surface of a belt of a vertebral endplate spreader to a first vertebra;
engaging a bottom surface of the belt of the vertebral endplate spreader to a second vertebra proximate to the first vertebra; and
distracting the first and second vertebrae from one another and translating the vertebrae laterally for correction of alignment of the first and second vertebrae, wherein distraction and translation are achieved by rotating the belt to move top and bottom surfaces of the belt in opposite directions from one another.

2. A method as recited in claim 1, wherein engaging top and bottom surfaces of the belt to the vertebrae include approaching the vertebrae with the vertebral endplate spreader from an anterior approach.

3. A method as recited in claim 1, wherein translating includes moving the superior of the two vertebrae in a posterior direction to correct a listhesis condition of the vertebrae.

4. A method as recited in claim 1, wherein translating includes moving the superior of the two vertebrae in an anterior direction to correct a retrolisthesis condition of the vertebrae.

5. A method as recited in claim 1, wherein engaging top and bottom surfaces of the belt to the vertebrae include approaching the vertebrae with the vertebral endplate spreader from a lateral approach.

6. A method as recited in claim 1, wherein translating includes moving the two vertebrae relative to one another in a lateral direction to correct a lateral slippage condition of the vertebrae related to scoliosis.

7. A method as recited in claim 1, further comprising inserting an implant between the first and second vertebrae, wherein the implant includes a bore therethrough having a bore entrance defined along a first axis and a bore exit defining a second axis that is angled with respect to the first axis to facilitate implantation of the implant.

8. A method as recited in claim 7, further comprising securing the implant to the respective endplates of the first and second vertebrae with a flexible screw for passing into the bore of the implant along the first axis and out of the bore of the implant along the second axis.

* * * * *